(12) United States Patent
McGowan et al.

(10) Patent No.: US 10,932,679 B2
(45) Date of Patent: Mar. 2, 2021

(54) PRESSURE SENSING GUIDEWIRES AND METHODS OF USE

(71) Applicant: BOSTON SCIENTIFIC SCIMED, INC., Maple Grove, MN (US)

(72) Inventors: Roger W. McGowan, Otsego, MN (US); Brice L. Shireman, Maple Grove, MN (US); Lloyd Radman, Blaine, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1226 days.

(21) Appl. No.: 14/656,441

(22) Filed: Mar. 12, 2015

(65) Prior Publication Data

US 2015/0265167 A1   Sep. 24, 2015

Related U.S. Application Data

(60) Provisional application No. 61/955,089, filed on Mar. 18, 2014.

(51) Int. Cl.
| | | |
|---|---|---|
| *A61B 5/0215* | (2006.01) | |
| *A61B 5/00* | (2006.01) | |
| *A61M 25/09* | (2006.01) | |
| *A61M 25/00* | (2006.01) | |

(52) U.S. Cl.
CPC ........ *A61B 5/02154* (2013.01); *A61B 5/0084* (2013.01); *A61B 5/6851* (2013.01); *A61M 25/09* (2013.01); *A61B 2562/0233* (2013.01); *A61B 2562/0247* (2013.01); *A61M 2025/0002* (2013.01); *A61M 2025/09091* (2013.01)

(58) Field of Classification Search
CPC ......... A61M 2025/09175; A61M 2025/09133; A61M 2025/0002; A61M 25/09; A61B 5/6852; A61B 2562/0247; A61B 2562/0233; A61B 5/6851; A61B 5/0084; A61B 5/02154
See application file for complete search history.

(56) References Cited

U.S. PATENT DOCUMENTS

| | | |
|---|---|---|
| 3,963,323 A | 6/1976 | Arnold |
| 4,771,782 A | 9/1988 | Millar |
| 4,953,553 A | 9/1990 | Tremulis |
| 5,106,455 A | 4/1992 | Jacobsen et al. |

(Continued)

FOREIGN PATENT DOCUMENTS

| | | |
|---|---|---|
| DE | 202014100938 U1 | 3/2014 |
| EP | 0235992 A1 | 9/1987 |

(Continued)

*Primary Examiner* — Bill Thomson
*Assistant Examiner* — Helene Bor
(74) *Attorney, Agent, or Firm* — Seager, Tufte & Wickhem, LLP

(57) ABSTRACT

A pressure sensing guidewire includes a distal end and a proximal end. The guidewire includes a tubular member having a distal portion and a proximal portion. The guidewire includes an optical pressure sensor disposed within the distal portion of the tubular member, and a polymer fiber optic cable extending proximally from the optical pressure sensor. The optical pressure sensor is located at a position that is about 3 centimeters or less from the distal end of the pressure sensing guidewire.

19 Claims, 3 Drawing Sheets

(56) References Cited

U.S. PATENT DOCUMENTS

| | | | |
|---|---|---|---|
| 5,135,503 A * | 8/1992 | Abrams | A61M 25/09 600/585 |
| 5,178,159 A | 1/1993 | Christian | |
| 5,238,004 A | 8/1993 | Sahatjian et al. | |
| 5,313,957 A | 5/1994 | Little | |
| 5,421,195 A | 6/1995 | Wlodarczyk | |
| 5,422,969 A | 6/1995 | Eno | |
| 5,427,114 A | 6/1995 | Colliver et al. | |
| 5,438,873 A | 8/1995 | Wlodarczyk et al. | |
| 5,573,520 A | 11/1996 | Schwartz et al. | |
| 5,633,963 A | 5/1997 | Rickenbach et al. | |
| 5,755,668 A | 5/1998 | Itoigawa et al. | |
| 5,772,609 A | 6/1998 | Nguyen et al. | |
| 5,797,856 A | 8/1998 | Frisbie et al. | |
| 5,872,879 A | 2/1999 | Hamm | |
| 5,902,248 A | 5/1999 | Millar et al. | |
| 5,938,624 A | 8/1999 | Akerfeldt et al. | |
| 5,949,929 A | 9/1999 | Hamm | |
| 6,112,598 A | 9/2000 | Tenerz et al. | |
| 6,120,457 A | 9/2000 | Coombes et al. | |
| 6,139,510 A | 10/2000 | Palermo | |
| 6,162,182 A | 12/2000 | Cole | |
| 6,167,763 B1 | 1/2001 | Tenerz et al. | |
| 6,196,980 B1 | 3/2001 | Akerfeldt et al. | |
| 6,248,083 B1 | 6/2001 | Smith et al. | |
| 6,265,792 B1 | 7/2001 | Granchukoff | |
| 6,394,986 B1 | 5/2002 | Millar | |
| 6,398,738 B1 | 6/2002 | Millar | |
| 6,409,677 B1 | 6/2002 | Tulkki | |
| 6,428,336 B1 | 8/2002 | Akerfeldt | |
| 6,508,803 B1 | 1/2003 | Horikawa et al. | |
| 6,565,514 B2 | 5/2003 | Svanerudh et al. | |
| 6,579,246 B2 | 6/2003 | Jacobsen et al. | |
| 6,585,660 B2 | 7/2003 | Dorando et al. | |
| 6,615,067 B2 | 9/2003 | Hoek et al. | |
| 6,663,570 B2 | 12/2003 | Mott et al. | |
| 6,766,720 B1 | 7/2004 | Jacobsen et al. | |
| 6,767,327 B1 | 7/2004 | Corl et al. | |
| 6,776,720 B2 | 8/2004 | Bartlett | |
| 6,908,442 B2 | 6/2005 | von Malmborg et al. | |
| 6,918,873 B1 | 7/2005 | Millar et al. | |
| 6,918,882 B2 | 7/2005 | Skujins et al. | |
| 6,974,422 B1 | 12/2005 | Millar | |
| 6,976,965 B2 | 12/2005 | Corl et al. | |
| 6,993,974 B2 | 2/2006 | Tenerz et al. | |
| 6,994,695 B1 | 2/2006 | Millar | |
| 7,071,197 B2 | 7/2006 | Leonardi et al. | |
| 7,134,994 B2 | 11/2006 | Alpert et al. | |
| 7,162,926 B1 | 1/2007 | Guziak et al. | |
| 7,187,453 B2 | 3/2007 | Belleville | |
| 7,259,862 B2 | 8/2007 | Duplain | |
| 7,265,847 B2 | 9/2007 | Duplain et al. | |
| 7,274,956 B2 | 9/2007 | Mott et al. | |
| 7,331,236 B2 | 2/2008 | Smith et al. | |
| 7,532,920 B1 | 5/2009 | Ainsworth et al. | |
| 7,618,379 B2 | 11/2009 | Reynolds et al. | |
| 7,684,657 B2 | 3/2010 | Donlagic et al. | |
| 7,689,071 B2 | 3/2010 | Belleville et al. | |
| 7,715,903 B2 | 5/2010 | Hartley et al. | |
| 7,724,148 B2 | 5/2010 | Samuelsson et al. | |
| 7,731,664 B1 | 6/2010 | Millar | |
| 7,759,633 B2 | 7/2010 | Duplain et al. | |
| 7,783,338 B2 | 8/2010 | Ainsworth et al. | |
| 7,878,984 B2 * | 2/2011 | Jacobsen | A61M 25/01 600/585 |
| 7,930,014 B2 | 4/2011 | Hueneckens et al. | |
| 7,946,997 B2 | 5/2011 | Hübinette | |
| 8,025,623 B1 | 9/2011 | Millar | |
| 8,029,447 B2 | 10/2011 | Kanz et al. | |
| 8,174,395 B2 | 5/2012 | Samuelsson et al. | |
| 8,216,151 B2 | 7/2012 | Smith | |
| 8,298,156 B2 | 10/2012 | Manstrom et al. | |
| 8,317,715 B2 | 11/2012 | Belleville et al. | |
| 8,343,076 B2 | 1/2013 | Sela et al. | |
| 8,393,802 B2 | 3/2013 | Stanley et al. | |
| 8,410,940 B2 | 4/2013 | Samuelsson et al. | |
| 8,461,997 B2 | 6/2013 | Samuelsson et al. | |
| 8,485,985 B2 | 7/2013 | Manstrom et al. | |
| 8,555,712 B2 | 10/2013 | Narvaez et al. | |
| 8,556,820 B2 | 10/2013 | Alpert et al. | |
| 8,562,537 B2 | 10/2013 | Alpert et al. | |
| 8,583,218 B2 | 11/2013 | Eberle | |
| 8,636,659 B2 | 1/2014 | Alpert et al. | |
| 8,641,633 B2 | 2/2014 | Smith | |
| 8,641,639 B2 | 2/2014 | Manstrom et al. | |
| 8,676,299 B2 | 3/2014 | Schmitt et al. | |
| 8,698,638 B2 | 4/2014 | Samuelsson et al. | |
| 8,752,435 B2 | 6/2014 | Belleville et al. | |
| 8,936,401 B2 | 1/2015 | Belleville et al. | |
| 8,998,823 B2 | 4/2015 | Manstrom et al. | |
| 9,052,466 B2 | 6/2015 | Belleville et al. | |
| 2002/0165600 A1 * | 11/2002 | Banas | A61F 2/91 623/1.11 |
| 2002/0183597 A1 * | 12/2002 | Kaufman | A61B 5/0031 600/300 |
| 2003/0069522 A1 | 4/2003 | Jacobsen et al. | |
| 2004/0073141 A1 | 4/2004 | Hartley et al. | |
| 2004/0181174 A2 | 9/2004 | Davis et al. | |
| 2005/0000294 A1 | 1/2005 | Tenerz et al. | |
| 2006/0122537 A1 | 6/2006 | Reynolds et al. | |
| 2008/0119758 A1 | 5/2008 | Samuelsson et al. | |
| 2009/0082678 A1 | 3/2009 | Smith | |
| 2009/0192412 A1 | 7/2009 | Sela et al. | |
| 2010/0145308 A1 | 6/2010 | Layman et al. | |
| 2010/0234698 A1 * | 9/2010 | Manstrom | A61B 5/02007 600/478 |
| 2010/0241008 A1 | 9/2010 | Belleville et al. | |
| 2011/0071407 A1 | 3/2011 | Hübinette et al. | |
| 2011/0178413 A1 | 7/2011 | Schmitt et al. | |
| 2011/0186294 A1 | 8/2011 | Narvaez et al. | |
| 2011/0319773 A1 | 12/2011 | Kanz et al. | |
| 2012/0227505 A1 | 9/2012 | Belleville et al. | |
| 2012/0265102 A1 | 10/2012 | Leo et al. | |
| 2013/0051731 A1 | 2/2013 | Belleville et al. | |
| 2013/0218032 A1 | 8/2013 | Belleville | |
| 2013/0296718 A1 | 11/2013 | Ranganathan et al. | |
| 2013/0317372 A1 | 11/2013 | Eberle et al. | |
| 2014/0005558 A1 * | 1/2014 | Gregorich | A61B 5/02154 600/480 |
| 2014/0058275 A1 | 2/2014 | Gregorich et al. | |
| 2014/0081244 A1 | 3/2014 | Voeller et al. | |
| 2014/0094697 A1 * | 4/2014 | Petroff | A61B 1/07 600/427 |
| 2014/0107624 A1 | 4/2014 | Belleville | |
| 2014/0121475 A1 | 5/2014 | Alpert et al. | |
| 2014/0180028 A1 * | 6/2014 | Burkett | A61B 5/02152 600/585 |
| 2014/0241669 A1 | 8/2014 | Belleville et al. | |
| 2014/0248021 A1 | 9/2014 | Belleville et al. | |
| 2015/0301288 A1 | 10/2015 | Thornton, Jr. | |

FOREIGN PATENT DOCUMENTS

| | | |
|---|---|---|
| EP | 0738495 A1 | 10/1996 |
| EP | 0879615 A1 | 11/1998 |
| EP | 0879617 A1 | 11/1998 |
| EP | 1479407 A1 | 11/2004 |
| WO | 9313707 A1 | 7/1993 |
| WO | 9553983 A1 | 12/1995 |
| WO | 9945352 A1 | 9/1999 |
| WO | 2008034010 A2 | 3/2008 |
| WO | 2011027282 A1 | 3/2011 |
| WO | 2011090744 A2 | 7/2011 |
| WO | 2011123689 A1 | 10/2011 |
| WO | 2012000798 A1 | 1/2012 |
| WO | 2012090210 A1 | 7/2012 |
| WO | 2013033489 A1 | 3/2013 |
| WO | 2014025255 A1 | 2/2014 |
| WO | 2015059311 A1 | 4/2015 |

* cited by examiner

PRESSURE SENSING GUIDEWIRES AND METHODS OF USE

CROSS-REFERENCE TO RELATED APPLICATIONS

This application claims priority under 35 U.S.C. § 119 to U.S. Provisional Application Ser. No. 61/955,089, filed Mar. 18, 2014, the entirety of which is incorporated herein by reference.

TECHNICAL FIELD

The present disclosure pertains to medical devices, and methods for using and manufacturing medical devices. More particularly, the present disclosure pertains to medical devices and methods that relate to pressure sensing guidewires.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

This disclosure provides design, material, manufacturing method, and use alternatives for medical devices. An example pressure sensing guidewire is disclosed. The pressure sensing guidewire has a distal end and a proximal end and comprises:

a tubular member having a distal portion and a proximal portion;

an optical pressure sensor disposed within the distal portion of the tubular member; and a polymer fiber optic cable extending proximally from the optical pressure sensor.

Alternatively or additionally to any of the embodiments above, the polymer fiber optic cable extends proximally to a proximal end of the pressure sensing guidewire.

Alternatively or additionally to any of the embodiments above, the polymer fiber optic cable extends proximally and is operably connected to a glass fiber optic that extends proximally to a proximal end of the pressure sensing guidewire.

Alternatively or additionally to any of the embodiments above, the distal portion of the tubular member forms a distal cap, and the optical pressure sensor is disposed within the distal cap.

Alternatively or additionally to any of the embodiments above, the distal cap includes one or more apertures permitting blood to enter an interior of the distal cap.

Alternatively or additionally to any of the embodiments above, the distal portion of the tubular member includes a shapeable structure.

Alternatively or additionally to any of the embodiments above, the pressure sensing guidewire further comprises a tubular member with a plurality of slots formed therein extending proximally from the distal cap.

Alternatively or additionally to any of the embodiments above, the pressure sensing guidewire further comprises a coil disposed over at least a portion of the tubular member with a plurality of slots formed therein.

Alternatively or additionally to any of the embodiments above, the pressure sensing guidewire further comprises a polymer sleeve disposed over at least a portion of the tubular member with a plurality of slots formed therein.

A pressure sensing guidewire is disclosed. The pressure sensing guidewire has a distal end and a proximal end and comprises:

a first tubular member having a distal portion and a proximal portion;

a second tubular member extending distally from the distal portion of the first tubular member, the second tubular member having a proximal end, a distal end and a plurality of slots formed therein;

a distal cap extending distally from the distal end of the second tubular member;

an optical pressure sensor disposed within the distal cap; and a polymer fiber optic cable extending proximally from the optical pressure sensor;

wherein the optical pressure sensor is located at a position that is less than about 3 centimeters from the distal end of the pressure sensing guidewire.

Alternatively or additionally to any of the embodiments above, the polymer fiber optic cable extends proximally to a proximal end of the pressure sensing guidewire.

Alternatively or additionally to any of the embodiments above, the polymer fiber optic cable extends proximally and is operably connected to a glass fiber optic that extends proximally to a proximal end of the pressure sensing guidewire.

Alternatively or additionally to any of the embodiments above, the distal cap includes one or more apertures permitting blood to enter an interior of the distal cap.

Alternatively or additionally to any of the embodiments above, the pressure sensing guidewire further comprises a coil disposed over at least a portion of the second tubular member.

Alternatively or additionally to any of the embodiments above, the pressure sensing guidewire further comprises a polymer sleeve disposed over at least a portion of the second tubular member.

A method of using a guidewire including a tubular member having a distal portion and a proximal portion, an optical pressure sensor disposed within the distal portion of the tubular member and a polymer fiber optic cable extending proximally from the optical pressure sensor is disclosed. The method comprises:

advancing the guidewire through a patient's vasculature to a position proximate a lesion; measuring a pressure proximal the lesion;

advancing the guidewire through the lesion such that the pressure sensor is distal the legion; and measuring a pressure distal the lesion.

Alternatively or additionally to any of the embodiments above, measuring a pressure proximal the lesion precedes advancing the guidewire through the lesion.

Alternatively or additionally to any of the embodiments above, the method further comprises, subsequent to advancing the guidewire through the lesion, withdrawing the guidewire prior to measuring a pressure proximal the legion.

Alternatively or additionally to any of the embodiments above, advancing the guidewire through the lesion comprises advancing the guidewire through the lesion such that a distal end of the guidewire extends past the lesion a distance of less than about 3 centimeters.

Alternatively or additionally to any of the embodiments above, the guidewire includes a shapeable distal portion, and the method further comprises shaping the shapeable distal portion prior to advancing the guidewire through a patient's vasculature to a position proximate a lesion.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The present disclosure may be more completely understood in consideration of the following detailed description of various embodiments of the present disclosure in connection with the accompanying drawings, in which.

Figure 1:
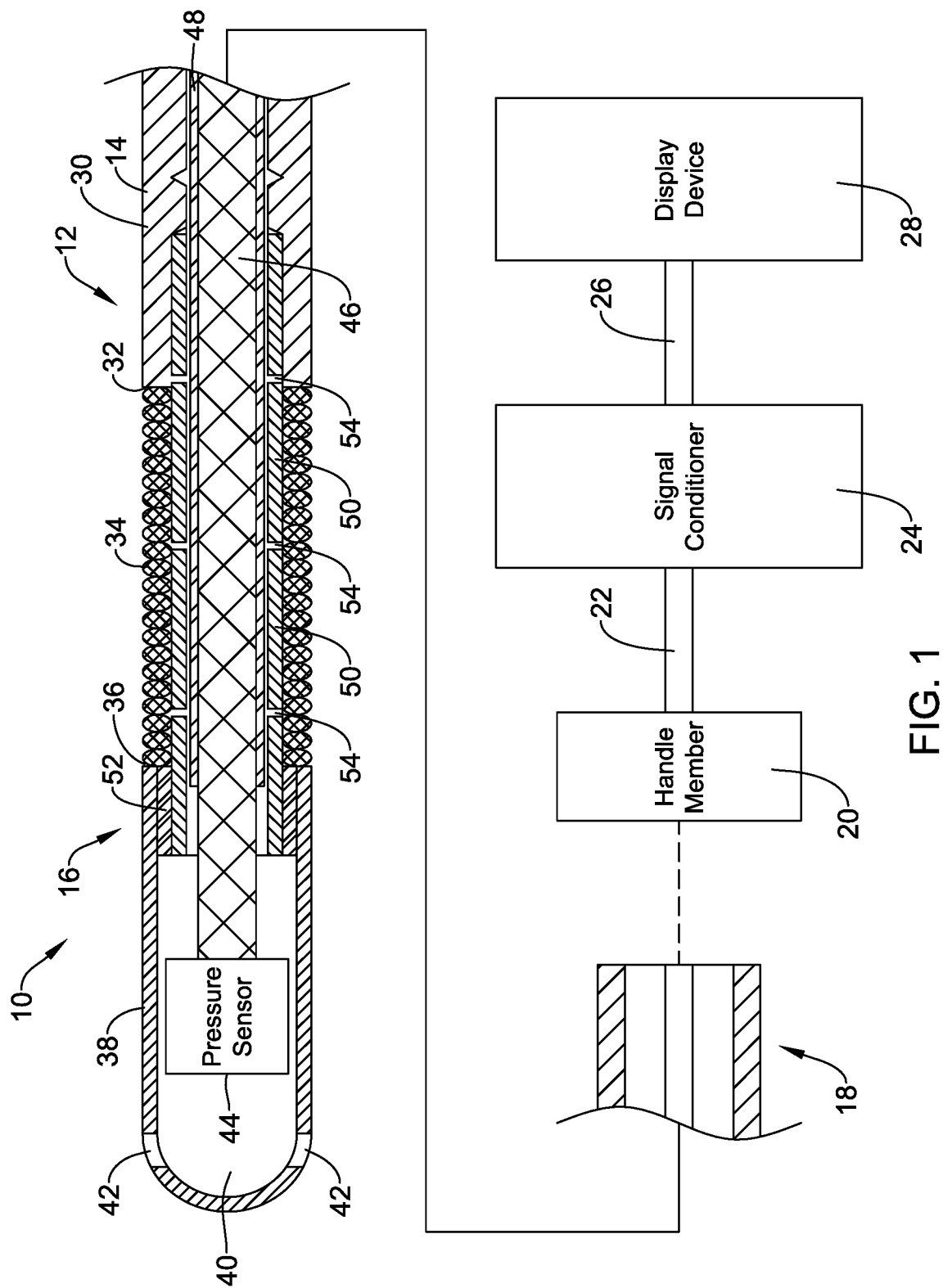
FIG. 1 is a schematic view of a system including a cross-sectional view of an example pressure sensing guidewire.

While the present disclosure is amenable to various modifications and alternative forms, specifics thereof have been shown by way of example in the drawings and will be described in detail. It should be understood, however, that the intention is not to limit the present disclosure to particular embodiments described. On the contrary, the intention is to cover all modifications, equivalents, and alternatives falling within the spirit and scope of the present disclosure.

DETAILED DESCRIPTION

Definitions of certain term are provided below, and these definitions shall be applied, unless a different definition is given in the claims or elsewhere in this specification.

All numeric values used herein are assumed to be modified by the term "about," whether or not explicitly indicated. The term "about" generally refers to a range of numbers that one of skill in the art would consider equivalent to the recited value (i.e., having the same or substantially the same function or result). In many instances, the terms "about" may include numbers that are rounded to the nearest significant figure. The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents, unless the content clearly dictates otherwise. As used in this specification and the appended claims, the term "or" is generally employed in its sense including "and/or", unless the content clearly dictates otherwise.

The following detailed description should be read with reference to the drawings in which similar elements in different drawings are identified with the same reference numbers. The drawings, which are not necessarily to scale, depict illustrative embodiments and are not intended to limit the scope of the invention.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure, or characteristic is described in connection with one embodiment, it should be understood that such feature, structure, or characteristic may also be used in connection with other embodiments, whether or not explicitly described, unless cleared stated to the contrary.

During some medical interventions, it may be desirable to measure and/or monitor the blood pressure within a blood vessel. For example, some medical devices may include pressure sensors that allow a clinician to monitor blood pressure. Such devices may be useful in determining fractional flow reserve (FFR), which may be understood as the pressure after a stenosis relative to the pressure before the stenosis. A number of pressure sensing devices, however, may pose technical challenges for steering, tracking, torqueing or otherwise navigating the device within the vasculature. For example, medical devices may include a relatively stiff pressure sensor located at or near the distal tip of the device and/or a sensor housing (in which the sensor is mounted) that may also be relatively stiff. Disclosed herein are a number of medical device that include pressure sensing capabilities and may be more easily steered, tracked, torqued, and/or otherwise navigated through the anatomy.

FIG. 1 is a schematic view of an example system 10 for obtaining pressure measurements within a patient's anatomy. In some examples, as illustrated, the system 10 includes a pressure sensing guidewire 12 having a guidewire shaft 14 that extends from a distal region 16 to a proximal region 18. At the proximal region 18, the pressure sensing guidewire 12 may be configured to be attached to a connector or handle member 20. Handle 20 may include a suitable connector for a cable 22 to be attached to handle 20 and extend to another suitable device such as an interferometer or signal conditioner 24. Signal conditioner 24 may include a light source and may be configured to process optical signals received at signal conditioner 24. Another cable 26 may, in some embodiments, extend from signal conditioner 24 to a suitable output device such as a display device 28, which may be configured to display information provided by signal conditioner 24.

Display device 28 may represent the ratio textually, graphically, or pictorially for diagnosing a medical condition within the body lumen. A clinician may utilize the readings from display device 28 to tailor the intervention to the needs of the patient or otherwise advance the goals of the intervention. These are just examples. It will be appreciated that other devices and/or arrangements may be utilized with pressure sensing guidewire 12.

Distal region 16 of pressure sensing guidewire 12 includes structure that facilitates use of pressure sensing guidewire 12. Guidewire shaft 14 includes a first tubular member 30. In some embodiments, as illustrated, first tubular member 30 extends a substantial length of the pressure sensing guidewire 12. First tubular member 30 terminates at a tubular member distal end 32. Distal region 16 includes a coil structure 34 that extends distally to a coil structure distal end 36. A distal cap 38 abuts the coil structure distal end 36 and completes the distal portion of pressure sensing guidewire 12. Distal cap 38 defines a void space 40. One or more apertures 42 extend through a wall forming distal cap 38, thereby providing fluid communication between void space 40 and the environment immediately outside of pressure sensing guidewire 12.

A pressure sensor 44 is disposed within the void space 40. By virtue of the aforementioned fluid communication afforded by the one or more apertures 42, the pressure sensor 44 is configured to obtain pressure measurements within the environment immediately outside of pressure sensing guidewire 12. While pressure sensor 44 is shown schematically in FIG. 1, it can be appreciated that the structural form and/or type of pressure sensor 44 may vary. For example, pressure sensor 44 may include a semiconductor (e.g., silicon wafer) pressure sensor, piezoelectric pressure sensor, a fiber optic or optical pressure sensor, a Fabry-Perot type pressure sensor, an ultrasound transducer and/or ultrasound pressure sensor, a magnetic pressure sensor, a solid-state pressure sensor, or the like, or any other suitable pressure sensor.

A clinician may use pressure sensing guidewire 12 to measure or calculate FFR (e.g., the pressure after an intravascular lesion relative to the pressure before the lesion). This may include taking an initial pressure reading before or upstream of the lesion and then a comparative reading after or downstream of the lesion. This may also include monitoring the pressure while advancing pressure sensing guidewire 12 through a blood vessel until a pressure differential or drop in pressure is observed, indicating that pressure sensing guidewire 12 has reached and/or partially past the lesion as well as monitoring increases in pressure during and/or following a treatment intervention. In some embodiments, a second pressure measuring device may be used to measure pressure at another intravascular location and this pressure may be utilized in the calculation of FFR or otherwise used as part of the intervention.

A fiber optic cable 46 is operably connected to pressure sensor 44 and extends proximally therefrom. In some embodiments, fiber optic cable 46 is a polymer fiber optic cable and may extend a length of guidewire shaft 14. In some embodiments, as will be discussed with respect to subsequent drawings, fiber optic cable 46 may include a distal section that is polymeric fiber optic cable and a proximal section that is glass fiber optic cable. In some embodiments, it is contemplated that fiber optic cable 46 may be a glass fiber optic cable over substantially all of its length. In some embodiments, at least a portion of fiber optic cable 46 may include optionally include a protective coating 48 extending a length of fiber optic cable 46.

In some embodiments, as illustrated, pressure sensing guidewire 12 may include a second tubular member 50. Second tubular member 50 may be joined to distal cap 38 via a connection schematically illustrated as connection 52. Connection 52 may represent adhesive, solder, a weld, or any other suitable connection mechanism. The second tubular member 50 forms part of the distal region 16 and in some embodiments may, in combination with the coil structure 34, contribute to a shapeability of the distal region 16. In some embodiments, the distal region 16 may be bent into a desired shape prior to being advanced through the vasculature. To aid in flexibility, in some embodiments second tubular member 50 includes several slots 54. While three slots 54 are illustrated, it will be appreciated that second tubular member 50 may include any number of slots 54. The relative size, number and spacing of slots 54 along second tubular member 50 may be varied in order to achieve a desired level of flexibility and shapeability.

Figure 2:
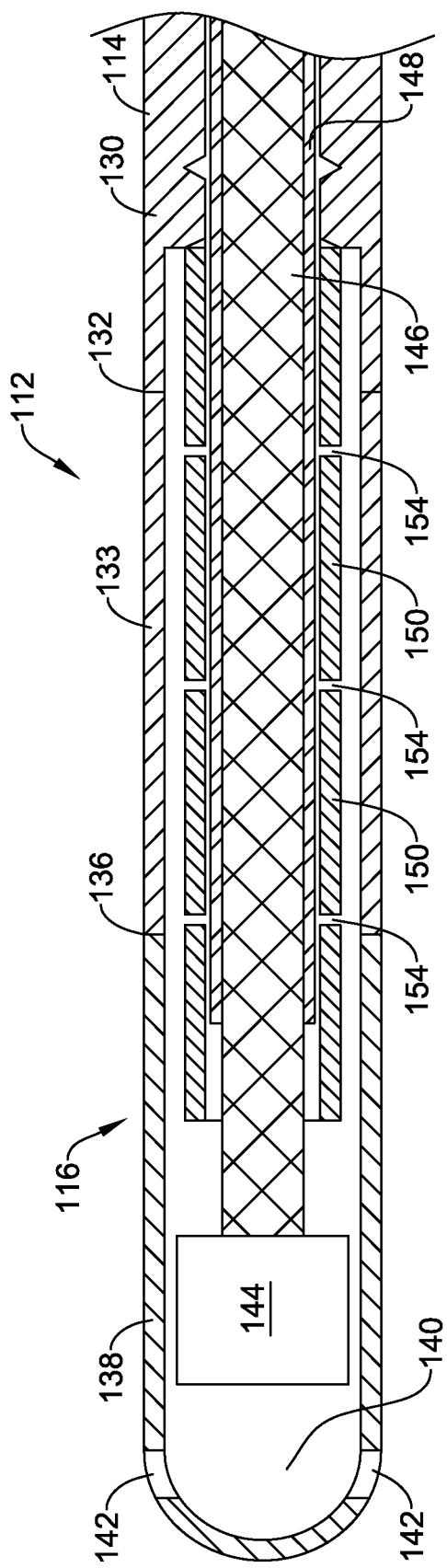
FIG. 2 is a cross-sectional view of another example pressure sensing guidewire.

FIG. 2 provides a schematic illustration of a distal region 116 of a pressure sensing guidewire 112. Pressure sensing guidewire 112 includes a guidewire shaft 114 that includes a first tubular member 130. In some embodiments, first tubular member 130 extends a substantial length of the pressure sensing guidewire 112. First tubular member 130 extends distally to a point 132. A polymer sleeve 133 extends distally from point 132 to a distal end 136. A distal cap 138 abuts the polymer sleeve 133 and completes the distal portion of pressure sensing guidewire 12. Distal cap 138 defines a void space 140. One or more apertures 142 extend through a wall forming distal cap 138, thereby providing fluid communication between void space 140 and the environment immediately outside of pressure sensing guidewire 112.

A pressure sensor 144 is disposed within the void space 140 and can be any suitable pressure sensor. By virtue of the aforementioned fluid communication afforded by the one or more apertures 142, the pressure sensor 144 is configured to obtain pressure measurements within the environment immediately outside of pressure sensing guidewire 112.

A fiber optic cable 146 is operably connected to pressure sensor 144 and extends proximally therefrom. In some embodiments, fiber optic cable 146 is a polymer fiber optic cable and may extend a length of guidewire shaft 114. In some embodiments, as will be discussed with respect to subsequent drawings, fiber optic cable 146 may include a distal section that is polymeric fiber optic cable and a proximal section that is glass fiber optic cable. In some embodiments, at least a portion of fiber optic cable 146 may include optionally include a protective coating 148 extending a length of fiber optic cable 146.

In some embodiments, as illustrated, pressure sensing guidewire 112 may include a second tubular member 150. The second tubular member 150 forms part of the distal region 116 and in some embodiments may contribute to a shapeability of the distal region 116. In some embodiments, the distal region 116 may be bent into a desired shape prior to being advanced through the vasculature. To aid in flexibility, in some embodiments second tubular member 150 includes several slots 154. While three slots 154 are illustrated, it will be appreciated that second tubular member 150 may include any number of slots 154. The relative size, number and spacing of slots 154 along second tubular member 150 may be varied in order to achieve a desired level of flexibility and shapeability.

In some embodiments, second tubular member 150 secures and aligns the fiber optic cable 146 along a central axis of first tubular member 130. In some embodiments, this central placement helps prevent pressure sensor 144 from contacting an internal surface of distal cap 138. Contact, if it were to occur, could cause offsets in measured fluid pressure.

As illustrated in FIGS. 1 and 2, pressure sensor 44 (FIG. 1) and pressure sensor 144 (FIG. 2) may be located relatively closer to a distal end of pressure sensing guidewire 12 (FIG. 1) and pressure sensing guidewire 112 (FIG. 2) than previous pressure sensing guidewires that utilize glass fiber optic cables. Because polymeric fiber optic cables are more flexible than glass fiber optic cables, the fiber optic cable can, in the illustrated embodiments, extend through a flexible, shapeable distal region 16, 116. Accordingly, pressure sensor 44, 144 may be located less than about 3 centimeters from a distal end of the pressure sensing guidewire 12, 112. In some embodiments, pressure sensor 44, 144 may be located less than about 2 centimeters from a distal end of the pressure sensing guidewire 12, 112. In some embodiments, pressure sensor 44, 144 may be located less than about 1 centimeter or less than about 0.5 centimeters from a distal end of the pressure sensing guidewire 12, 112.

Alternatively, and in some embodiments, pressure sensor 44, 144 may be located at a relatively more proximal location. For example, in some embodiments, the pressure sensor 44, 144 may be disposed at a location that is as much as 30 centimeters from a distal end of pressure sensing guidewire 12, 112. In some instances, the pressure sensor 44, 144 may be disposed at a location that is about 10 to 15 centimeters from a distal end of pressure sensing guidewire 12, 112. It will be appreciated that in some embodiments, moving pressure sensor 44, 144 to a relatively more proximal location will enable the distal portions of pressure sensing guidewire 12, 112 to be made even more flexible, particularly in portions distal of pressure sensor 44, 144. In some embodiments, it will be appreciated that fiber optic cable 46, 146, particularly if polymer fiber optic cable, may function as an emergency tether, enabling retrieval of pressure sensing guidewire 12, 112.

As noted above, in some embodiments fiber optic cable 46, 146 may be a polymeric fiber optic cable that extends all the way or substantially all of the way through pressure sensing guidewire 12, 112. This provides enhanced flexibility, but as polymeric fiber optic cables do not conduct light as well as glass fiber optics, light losses can be higher than would be achieved using a glass fiber optic cable. However, as long as the losses are repeatable, the losses can be overcome, for example, by increasing the intensity of light originating from a light source. In some embodiments, fiber optic cable 46, 146 can include a distal portion that is polymeric and a proximal portion that is glass, thereby permitting greater flexibility and shapeability in the distal region 16, 116 of pressure sensing guidewire 12, 112 while reducing overall light losses. In some embodiments, fiber optic cable 46, 146 may be glass fiber optic cable that extends all the way or substantially all of the way through pressure sensing guidewire 12, 112.

Figure 3:
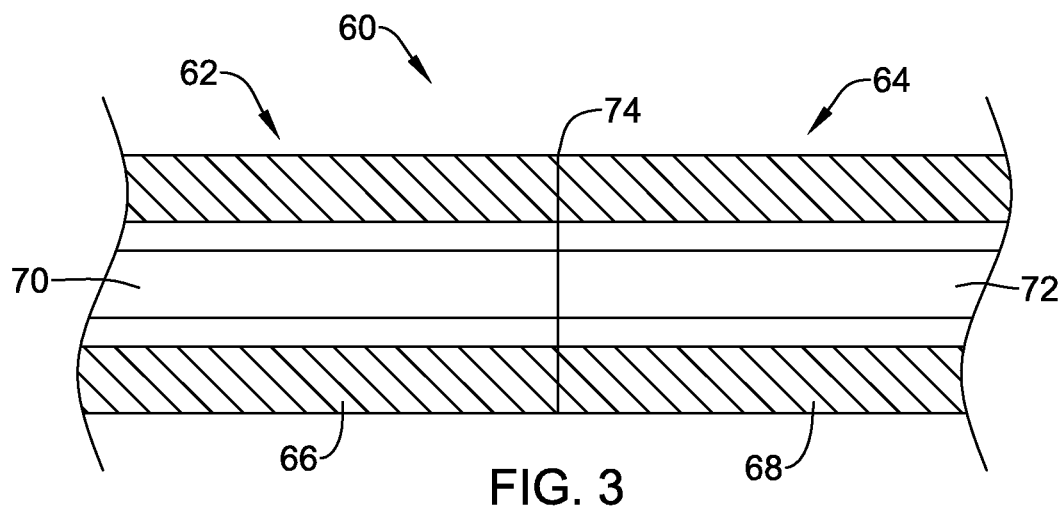
FIG. 3 is a cross-sectional view of a portion of another example pressure sensing guidewire.

FIG. 3 schematically illustrates a portion of a guidewire 60 that includes a distal portion 62 and a proximal portion 64. As illustrated, distal portion 62 and proximal portion 64 have a constant cross-sectional profile. Distal portion 62 includes a guidewire shaft 66 while proximal portion 64 includes a guidewire shaft 68. A distal fiber optic cable 70 extends through distal portion 62 and a proximal fiber optic cable 72 extends through proximal portion 64. Distal portion 62 meets proximal portion 64 at a connector 74. In some embodiments, distal fiber optic cable 70 is a polymeric fiber optic cable while proximal fiber optic cable 72 is a glass fiber optic cable.

As schematically illustrated, connector 74 generally represents a connection between distal portion 62 and proximal portion 64. In some embodiments, connector 74 may represent a simple butt joint between distal portion 62 and proximal portion 64, perhaps including a suitable adhesive. In some embodiments, however, connector 74 schematically represents a connector assembly, as illustrated in FIG. 4.

Figure 4:
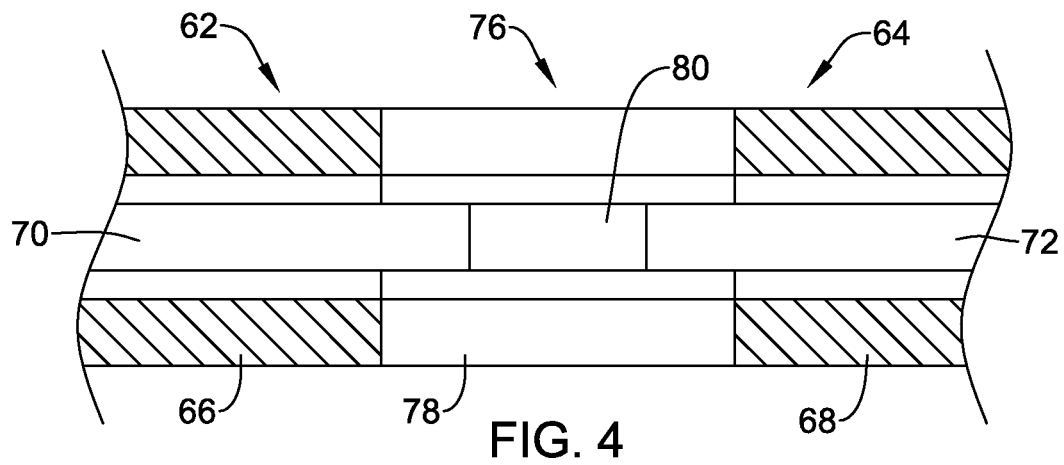
FIG. 4 is an enlarged view of a portion of FIG. 3.

FIG. 4 represents an enlarged view of FIG. 3, showing connector 74 manifested as a connector assembly 76. As illustrated, connector assembly 76 includes an outer portion 78 that is configured to join guidewire shaft 66 and guidewire shaft 68. In some embodiments, guidewire shaft 66 and guidewire shaft 68 may extend partially into outer portion 78 and may be adhesively or frictionally secured therein. Connector assembly 76 includes a fiber optic segment 80 that is configured to optically couple to A distal fiber optic cable 70 and to proximal fiber optic cable 72. Connector 76 may be configured to releasably secure guidewire shaft 66 and guidewire shaft 68 together. In some embodiments, connector 76 may be configured to provide what is intended to be a permanent connection, i.e., for the useable life of guidewire shaft 60.

Figure 5:
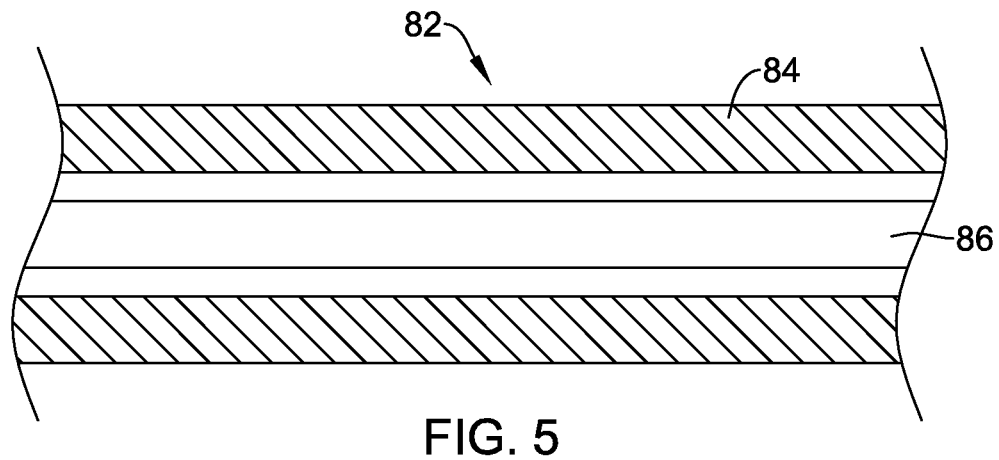
FIG. 5 is a cross-sectional view of a portion of another example pressure sensing guidewire.

FIG. 5 schematically illustrates a portion of a guidewire 82. Guidewire 82 includes an outer guidewire shaft portion 84 and a fiber optic cable 86 extending through outer guidewire shaft portion 84. In the illustrated embodiment, fiber optic cable 86 is a polymeric fiber optic cable. In some embodiments, the polymeric fiber optic cable extends essentially a length of the guidewire 82.

During operation, pressure sensing guidewire 12, 112 may be advanced through a patient's vasculature. In some embodiments, pressure sensing guidewire 12, 112 may be advanced into the vasculature via a catheter (not shown). In some embodiments, distal region 16, 116 may be shaped prior to insertion. Pressure sensing guidewire 12, 112 may be advanced such that the distal end of pressure sensing guidewire 12, 112 may be positioned proximate to a lesion. Once positioned, signal conditioner 24 may be activated to generate optical signals from a light source. The generated optical signals are guided through the polymer fiber optic cable 46, 146 to pressure sensor 44, 144 for measuring pressure of fluids proximal the lesion within the vasculature. In some embodiments, pressure sensing guidewire 12, 112 may be advanced through the lesion such that pressure sensor 44, 144 is distal to the lesion and another pressure measurement may be taken. The signal conditioner 24 may be operated to send the optical signals to the pressure sensor 44, 144 and receive the optical signals reflected by the pressure sensor 44, 144 for measuring pressure of fluids based on the optical signals within the vasculature.

A ratio of the fluid pressure measured proximal to the lesion and the fluid pressure distal to the lesion may be determined by signal conditioner 24 and displayed on display device 28 for determining the pressure gradient about the lesion within the vasculature. The determined pressure gradient may be used for diagnosing a medical condition with the vasculature. Once at least one of the fluid pressure proximal to the lesion, the fluid pressure distal to the lesion and the pressure gradient about the lesion within the vasculature are determined, pressure sensing guidewire 12, 112 may be withdrawn from the vasculature. However in some embodiments, after pressure sensing guidewire 12 is advanced through the lesion, pressure sensing guidewire 12, 112 may be withdrawn prior to measuring the fluid pressure either distal or again proximal to the lesion from the vasculature.

In some embodiments, tubular member 34, 133 may be a polymer or metallic sleeve made from a suitable polymeric material or a metal. Examples of the polymeric material may include, but not limited to, polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-£-isobutylene-£-styrene) (for example, SIBS and/or SIBS 50A), polycarbonates, ionomers, biocompatible polymers, other suitable materials, or mixtures, combinations, copolymers thereof, polymer/metal composites, and the like. In some embodiments, t first tubular member 30, 130 may be blended with a liquid crystal polymer (LCP), for example, up to about 6 wt-% LCP.

In some of these as well as other embodiments, tubular member 34, 133 may include a radiopaque material. In other words, tubular member 34, 133 may be made from a polymer loaded with the radiopaque material for tracking the guidewire 102 within the body lumen. For example, tubular member 34, 133 or one or more discrete portions thereof may include about 50-95 wt-% or about 75-95 wt-% radiopaque material with the balance being polymeric. In some embodiments, the radiopaque material may include tungsten. Other materials and/or arrangements may also be used. By virtue of including a radiopaque material in tubular member 34, 133, the pressure sensing guidewire 12, 112 may be manufactured without having additional radiopaque marker bands or radiopaque marker coils coupled thereto, for example, at a distal end of the pressure sensing guidewire 12, 112. In other embodiments, however, tubular member 34, 133 may include such radiopaque structures.

Second tubular member 50, 150 and/or distal cap 38, 128 may be made from a metal, metal alloy, polymer (some examples of which are disclosed above), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); nickel-cobalt-chromium-molybdenum alloys (e.g., UNS: R30035 such as MP35-N® and the like), platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of second tubular member 50, 150 and/or distal cap 38, 128 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of pressure sensing guidewire 12, 112 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated to achieve the same result.

In some embodiments, a degree of Magnetic Resonance Imaging (MRI) compatibility is imparted into pressure sensing guidewire 12, 112. For example, pressure sensing guidewire 12, 112 or portions thereof may be made of a material that does not substantially distort the image and create substantial artifacts (i.e., gaps in the image). Certain ferromagnetic materials, for example, may not be suitable because they may create artifacts in an MRI image. Pressure sensing guidewire 12, 112, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Other embodiments of the present disclosure will be apparent to those skilled in the art from consideration of the specification and practice of the embodiments disclosed herein. It is intended that the specification and examples be considered as exemplary only, and departure in form and detail may be made without departing from the scope and spirit of the present disclosure as described in the following claims.

What is claimed is:

1. A pressure sensing guidewire having a distal end and a proximal end, the pressure sensing guidewire comprising:
   a first tubular member having a distal portion and a proximal portion, the distal portion forming a distal cap having an inner surface;
   a second tubular member disposed within the first tubular member, the second tubular member having a constant diameter over its length and comprising a plurality of flexibility-enhancing slots formed therein;
   an optical pressure sensor disposed within the distal cap, wherein the optical pressure sensor includes a Fabry-Perot pressure sensor; and
   a polymer fiber optic cable extending proximally from the optical pressure sensor and through the second tubular member, the optical pressure sensor disposed at a distal end of the polymer fiber optic cable;
   wherein the second tubular member limits radial movement of the polymer fiber optic cable relative to the first tubular member and thus protects the optical pressure sensor from contacting the inner surface of the distal cap when the pressure sensing guidewire is subjected to bending.

2. The pressure sensing guidewire of claim 1, wherein the polymer fiber optic cable extends proximally to a proximal end of the pressure sensing guidewire.

3. The pressure sensing guidewire of claim 1, wherein the polymer fiber optic cable extends proximally and is operably connected to a glass fiber optic that extends proximally to a proximal end of the pressure sensing guidewire.

4. The pressure sensing guidewire of claim 1, wherein the distal cap includes one or more apertures permitting blood to enter an interior of the distal cap.

5. The pressure sensing guidewire of claim 1, wherein the distal portion of the tubular member includes a shapeable structure.

6. The pressure sensing guidewire of claim 1, wherein the second tubular member extends proximally from the distal cap.

7. The pressure sensing guidewire of claim 6, further comprising a coil disposed over at least a portion of the second tubular member.

8. The pressure sensing guidewire of claim 6, further comprising a polymer sleeve disposed over at least a portion of the second tubular member.

9. A pressure sensing guidewire having a distal end and a proximal end, the pressure sensing guidewire comprising:
   a first tubular member having a distal portion and a proximal portion;
   a constant diameter cylindrical second tubular member extending distally from the distal portion of the first tubular member, the second tubular member having a proximal end, a distal end and a plurality of slots formed therein;
   a distal cap extending distally from the distal end of the second tubular member;
   an optical pressure sensor disposed within the distal cap, wherein the optical pressure sensor includes a Fabry-Perot pressure sensor; and
   a polymer fiber optic cable extending proximally from the optical pressure sensor;
   wherein the optical pressure sensor is disposed within the distal cap at a position that is less than 3 centimeters from the distal end of the pressure sensing guidewire, and wherein the optical pressure sensor is constrained from contacting the distal cap by the second tubular member constraining radial movement of the polymer fiber optic cable relative to the first tubular member.

10. The pressure sensing guidewire of claim 9, wherein the polymer fiber optic cable extends proximally to a proximal end of the pressure sensing guidewire.

11. The pressure sensing guidewire of claim 9, wherein the polymer fiber optic cable extends proximally and is operably connected to a glass fiber optic that extends proximally to a proximal end of the pressure sensing guidewire.

12. The pressure sensing guidewire of claim 9, wherein the distal cap includes one or more apertures permitting blood to enter an interior of the distal cap.

13. The pressure sensing guidewire of claim 9, further comprising a coil disposed over at least a portion of the second tubular member.

14. The pressure sensing guidewire of claim 9, further comprising a polymer sleeve disposed over at least a portion of the second tubular member.

15. A method of using a guidewire including a first tubular member having a distal portion and a proximal portion, the distal portion forming a distal cap having an inner surface, an optical pressure sensor disposed within the distal portion of the first tubular member and a polymer fiber optic cable extending proximally from the optical pressure sensor, wherein the optical pressure sensor includes a Fabry-Perot pressure sensor, the optical pressure sensor constrained against contacting the inner surface of the distal cap via a constant diameter cylindrical second tubular member disposed within the first tubular member with the polymer fiber optic cable extending therethrough, the constant diameter cylindrical second tubular member comprising a plurality of flexibility-enhancing slots formed therein, the method comprising:

advancing the guidewire through a patient's vasculature to a position proximate a lesion;

measuring a pressure proximal the lesion;

advancing the guidewire through the lesion such that the pressure sensor is distal the lesion; and measuring a pressure distal the lesion.

16. The method of claim 15, wherein measuring a pressure proximal the lesion precedes advancing the guidewire through the lesion.

17. The method of claim 15, further comprising, subsequent to advancing the guidewire through the lesion, withdrawing the guidewire prior to measuring a pressure proximal the lesion.

18. The method of claim 15, wherein advancing the guidewire through the lesion comprises advancing the guidewire through the lesion such that a distal end of the guidewire extends past the lesion a distance of less than 3 centimeters.

19. The method of claim 15, wherein the guidewire includes a shapeable distal portion, and the method further comprises shaping the shapeable distal portion prior to advancing the guidewire through a patient's vasculature to a position proximate a lesion.

\* \* \* \* \*